United States Patent [19]
Li et al.

[11] Patent Number: 5,767,134
[45] Date of Patent: Jun. 16, 1998

[54] PRODRUG FORMS OF RIBONUCLEOTIDE REDUCTASE INHIBITORS 3-AP AND 3-AMP

[75] Inventors: Jun Li, Hamden; Chuan-Sheng Niu, Cheshire; Xiuyan Li, New Haven; Terrence W. Doyle, Killingworth; Shu-Hui Chen, Hamden, all of Conn.

[73] Assignee: Vion Pharmaceuticals, Inc., New Haven, Conn.

[21] Appl. No.: 856,568

[22] Filed: May 15, 1997

[51] Int. Cl.$^6$ .................... A61K 31/44; C07D 213/02
[52] U.S. Cl. .................................. 514/353; 546/306
[58] Field of Search .............................. 546/306; 514/353

[56] References Cited

U.S. PATENT DOCUMENTS

| | | | |
|---|---|---|---|
| 4,385,055 | 5/1983 | Klayman et al. | 424/248.4 |
| 4,447,427 | 5/1984 | Klayman et al. | 424/244 |
| 4,696,938 | 9/1987 | Le | 514/343 |

Primary Examiner—Zinna Northington Davis
Attorney, Agent, or Firm—Henry D. Coleman; R. Neil Sudol

[57] ABSTRACT

The present invention relates to novel prodrug forms of ribonucleoside diphosphate reductase inhibitors 3-aminopyridine-2-carboxaldehyde thiosemicarbazone (3-AP) 3-amino-4-methylpyridine-2-carboxaldehyde thiosemicarbazone (3-AMP) which have increased water solubility, bioavailablity and resistance to in vivo acetylation of their amino functions. Novel compounds according to the present invention relate to those of the formula:

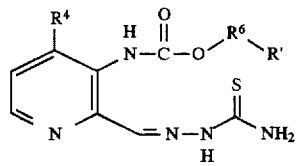

where
$R^4$ is H or $CH_3$ and
$R^5$ is CHR, benzyl or ortho or para substituted benzyl;
R is H, $CH_3$, $CH_2CH_3$, $CH_2CH_2CH_3$ or

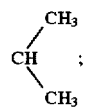

R' is a free acid phosphate, phosphate salt or an —S—S—R" group;
R" is $CH_2CH_2NHR^6$, $CH_2CH_2OH$, $CH_2COOR^7$, an ortho or para substituted alkylphenyl and ortho or para substituted nitro-phenyl;
$R^6$ is H, $C_1$–$C_4$ acyl group, trifluoroacetyl, benzoyl or substituted benzoyl group, and
$R^7$ is H, $C_1$–$C_4$ alkyl or a benzyl or substituted benzyl.

21 Claims, 11 Drawing Sheets

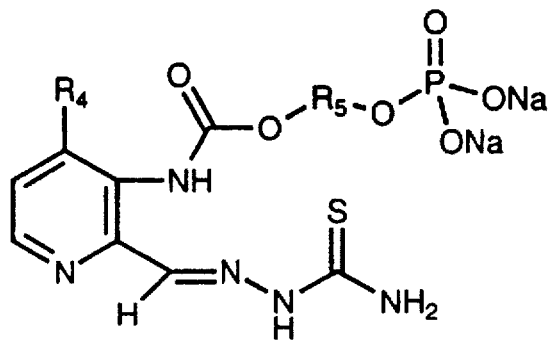
Where R⁴ is H or CH₃, and
R⁵ is CHR, or 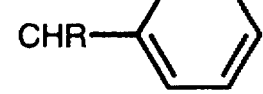
R is H or Me, Et, n-Pr, i-Pr, etc.
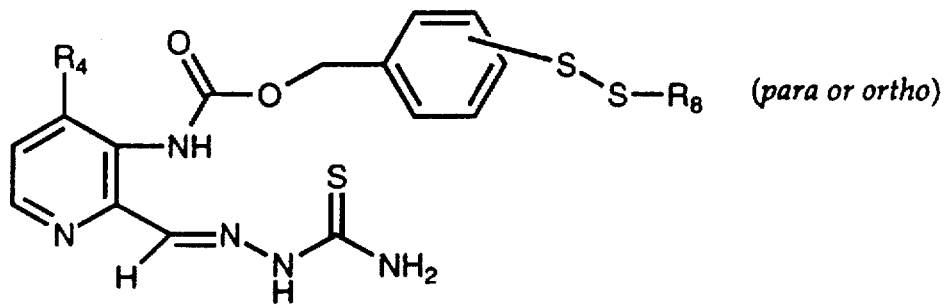
Where R⁴ is H or CH₃, and
R⁸ is $CH_2CH_2NH_2$, $CH_2CH_2NHAc$, $CH_2CH_2OH$, $CH_2CO_2H$ Figure 9. 3-AP and Prodrug I (para) incubated with rat liver S9
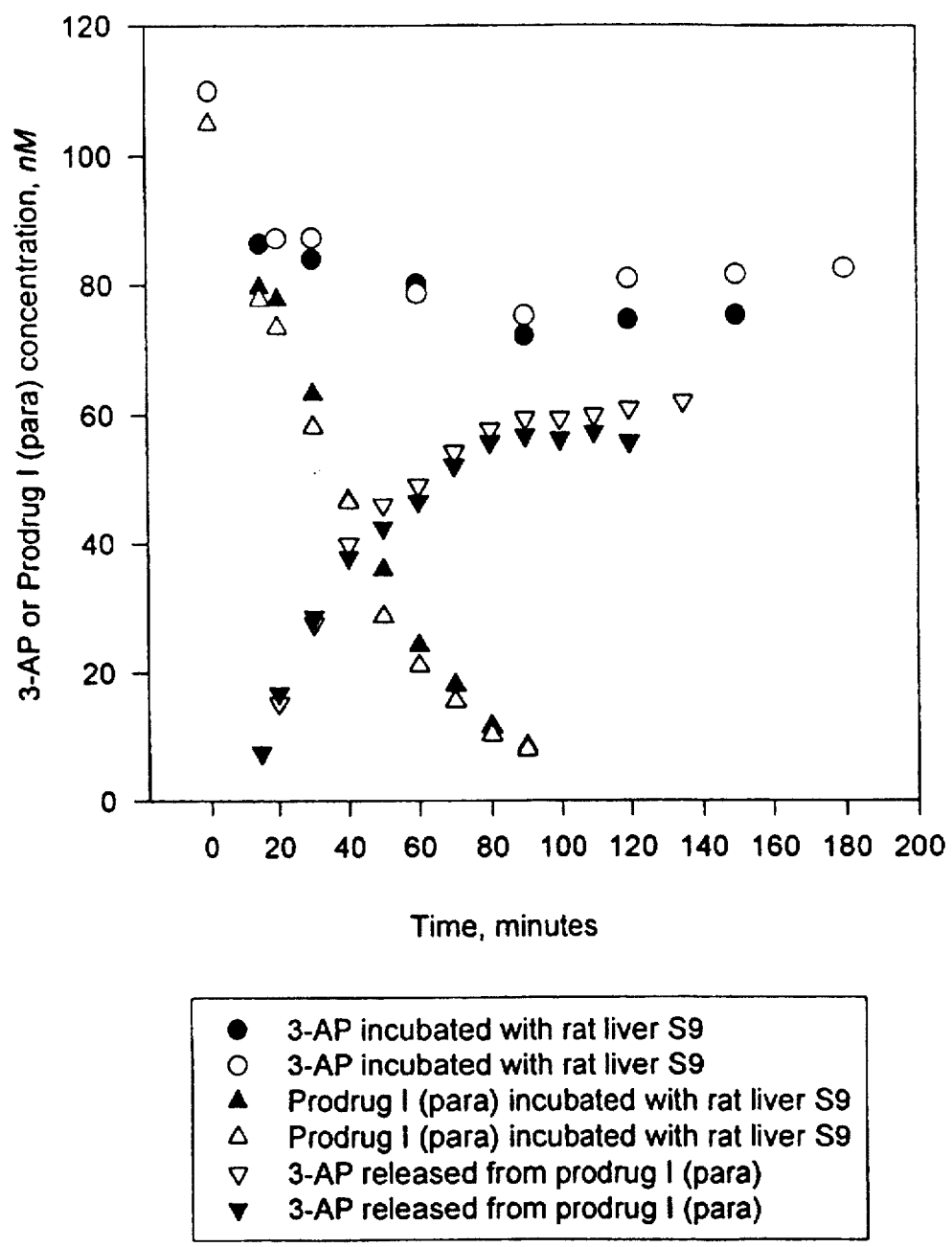
- ● 3-AP incubated with rat liver S9
- ○ 3-AP incubated with rat liver S9
- ▲ Prodrug I (para) incubated with rat liver S9
- △ Prodrug I (para) incubated with rat liver S9
- ▽ 3-AP released from prodrug I (para)
- ▼ 3-AP released from prodrug I (para)

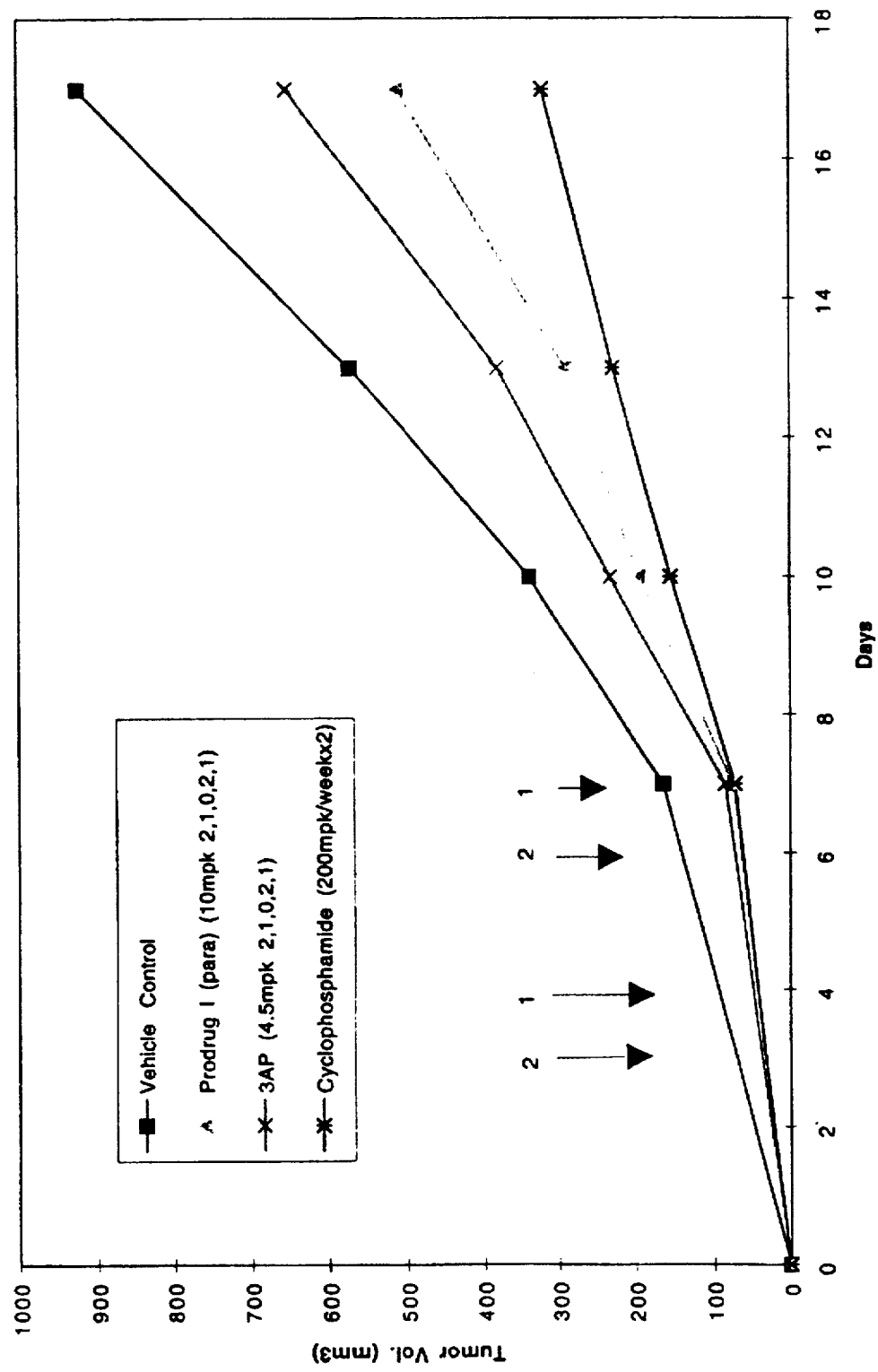
Figure 10  Anti-tumor Effects of Prodrug I (para) Disodium Salt on M109 in Balb/c Mice

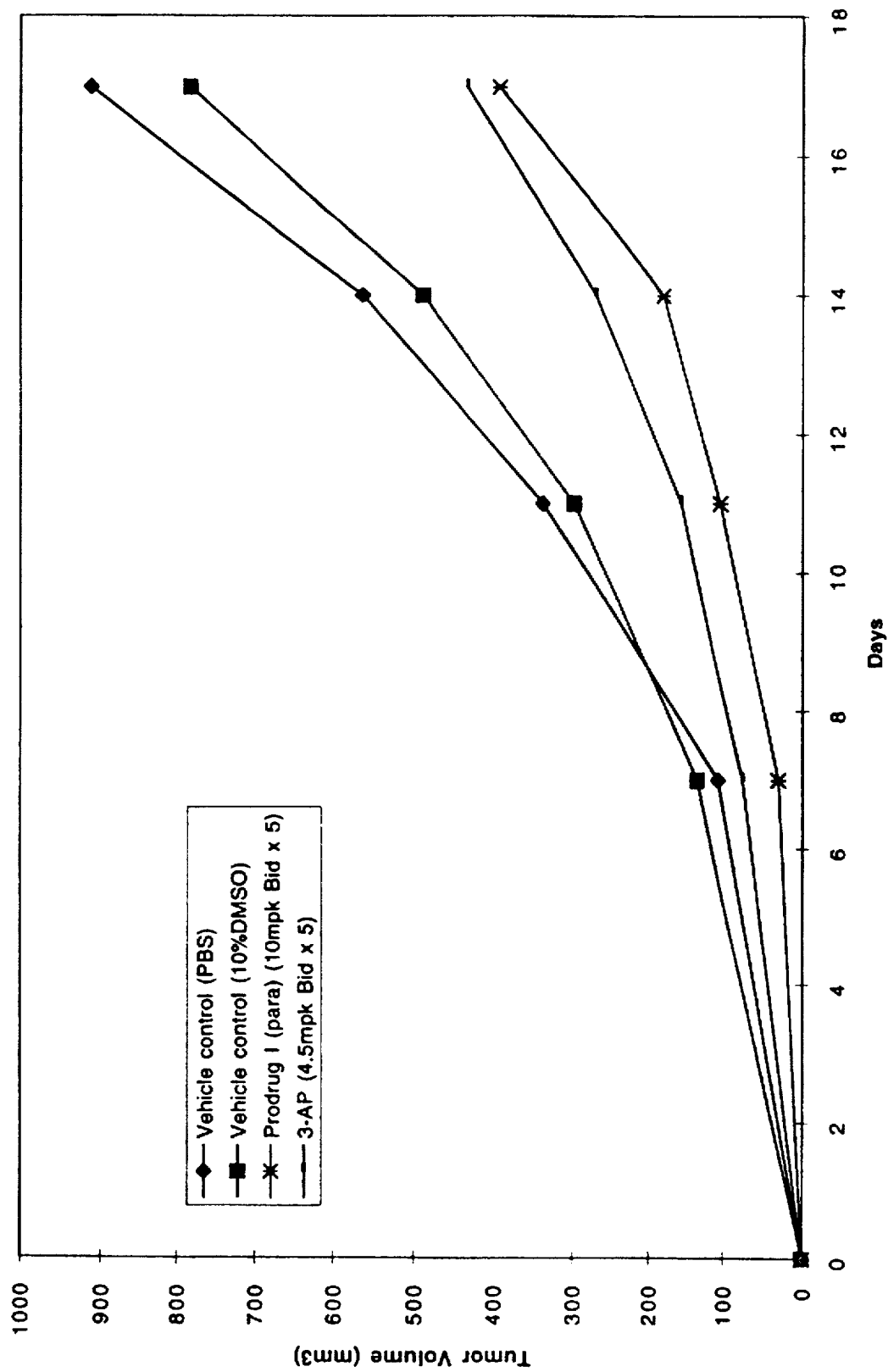

PRODRUG FORMS OF RIBONUCLEOTIDE REDUCTASE INHIBITORS 3-AP AND 3-AMP

FIELD OF THE INVENTION

The present invention relates to novel prodrug forms of ribonucleotide reductase inhibitors having increased water solubility, bioavailability and resistance to in vivo metabolic inactivation and their use in the treatment of cancer and/or tumors.

BACKGROUND OF THE INVENTION

Cancer is one of the leading causes of death known today, and effective treatment of many solid tumors remains elusive. It is believed that novel antitumor drugs possessing a strong inhibitory effect on ribonucleotide reductase, an essential enzyme for cellular replication, would be a useful addition to present drug regimens for treating cancer.

It is well-known that the reductive conversion of ribonucleotides to the corresponding deoxyribonucleotides is a key step in the biosynthesis of DNA. Since deoxyribonucleotides are present in extremely low levels in mammalian cells, investigators have assumed that an inhibitor of ribonucleotide reductase could be more effective than an inhibitor of DNA polymerase in blocking DNA synthesis. See, Cory and Chiba, "Combination Chemotherapy Directed at the Components of Nucleoside Diphosphate Reductase", *Inhibitors of Ribonucleoside diphosphate reductase Activity*, Cory, J. G. and Cory, A. M. Eds.; Pergamon Press: Oxford, 1989; pp 245–264. Consequently, through this work it was believed that the development of strong inhibitors of ribonucleotide reductase would create potential powerful weapons against cancer.

For many years, studies of novel α-(N)-heterocyclic carboxaldehyde thiosemicarbazones (HCTs), a class of the most potent inhibitors of ribonucleoside diphosphate reductase, has attracted considerable interest. A variety of HCTs such a 5-hydroxypyridine-2-carboxaldehyde thiosemicarbazone (5 HP), 4-methyl-5-amino-1-formylisoquinoline thiosemicarbazone (MAIQ-1), 5-(acetylamino)pyridine-2-carboxaldehyde thiosemicarbazone (5-AAP), 3- and 5-aminopyridine-2-carboxaldehyde thiosemicarbazone (3-AP and 5-AP) and their 4-methyl derivatives (3-AMP and 5-AMP), 3- and 5-hydroxy-4-methylpyridine-2-carboxaldehyde thiosemicarbazone (3-HMP and 5-HMP), have been reported. See, DeConti, et al., *Cancer Res.*, 1972, 32, 1455–1462; Agrawal, et al., *J. Med. Chem.* 1976, 19, 970–972; French, et al., *J. Med. Chem.*, 1974, 17, 172–181; Liu, et al., J. Med. Chem. 1992, 35, 3672–3677; Wang, et al., *J. Med. Chem.* 1992, 35, 3667–3671.

Structure-activity relationship studies of a series of HCTs revealed that both 3-AP and 3-AMP showed much better therapeutic effects against L1210 leukemia, M- 109 lung carcinoma and A2780 human ovarian carcinoma than other HCTs reported to date. Liu, et al., *J. Med. Chem.* 1992, 35, 3672–3677; Agrawal, et al., "The Chemistry and Biological Activity of the α-(N)-Heterocyclic Carboxaldehyde Thiosemicarbazones." *Progress in Medicinal Chemistry;* Ellis, G. P.; West, G. B., Eds.; Elsevier/North-Holland Biomedical Press: New York, 1978; Vol. 15. pp 321–356. In addition, 3-AP and 3-AMP are potent agents with significant antineoplastic activity in comparison with hydroxyurea (HU), an approved ribonucleotide reductase inhibitor used in clinics.

Despite the in vivo activity displayed by 3-AP and 3-AMP, the therapeutic potential of these new lead compounds in the HCT series may be limited by their limited water-solubility and bioavailability. Liu, et al., *J. Med. Chem.*, 1992, 35, 3672. In addition, N-acetylation of the amino function of 3-AP and 3-AMP represents a potential problematic metabolic pathway for the inactivation of these antitumor agents. Id. To address these issues, the present invention is, therefore, directed to several water-soluble prodrugs of 3-AP and 3-AMP. These include the phosphate-containing prodrugs.

OBJECTS OF THE INVENTION

It is an object of the invention to provide water-soluble prodrug forms of 3-AP and 3-AMP in order to increase the concentration of 3-AP and 3-AMP which can be delivered to a site of activity within a patient.

It is an additional object of the invention to provide prodrug forms of 3-AP and 3-AMP which increase their bioavailability.

It is a further object of the invention to provide prodrug forms of 3 -AP and 3-AMP which decrease in vivo acetylation of their amino functions.

It is yet another object of the invention to provide a method of treating neoplasia in animal or human patients utilizing the prodrug compounds of the instant invention.

BRIEF DESCRIPTION OF THE INVENTION

The present invention relates to prodrug forms of 3-aminopyridine-2-carboxyaldehyde thiosemicarbazone (3-AP) and 3-amino-4-methylpyridine-2-carboxaldehyde thiosemicarbazone (3-AMP) which have increased water solubility, bioavailablity, and resistance to metabolic inactivation. In prodrug forms of 3-AP and 3-AMP, which are significantly more soluble than are 3-AP and 3-AMP, the 3-amino group of 3-AP or 3-AMP is derivatized to a methyl or urethane moiety, preferably urethane, which is substituted with an organophosphate group or a disulfide group as shown in FIG. 1. The phosphate-containing prodrugs were designed to give good water-solubility at neutral pHs and increase bioavailability. The water-soluble disulfide prodrugs may be selectively activated in tumor cells having elevated levels of glutathione and/or glutathione S-transferase, thereby exploiting a known method of tumor multidrug resistance. In all cases, the carbamoyl prodrug linker serves as a temporary protecting group for the 3-amino substituent of the parent drugs. 3-AP and 3-AMP, making these prodrugs less likely to undergo metabolic inactivation through N-acetylation.

The prodrugs of the present invention are useful in the treatment of neoplasia in animal or human patients. In vivo, these prodrugs are metabolized to produce the active therapeutic agents 3-AP or 3-AMP. Comparisons between administration of the instant prodrugs and the parent therapeutic agents to combat the growth of solid tumors in mammals demonstrate the increased efficacy of the prodrugs. Particularly preferred embodiments of the prodrugs of the invention include prodrugs I and II, below, which are organophosphate derivatives of 3-AP, the organophosphate group being linked to 3-AP through a urethane moiety at the 3-amino position; and prodrug III, which is a disulfide derivative of 3-AP, the disulfide group being linked to 3-AP through a urethane moiety at the 3-amino position. Also preferred are the analogous prodrug forms of 3-AMP.

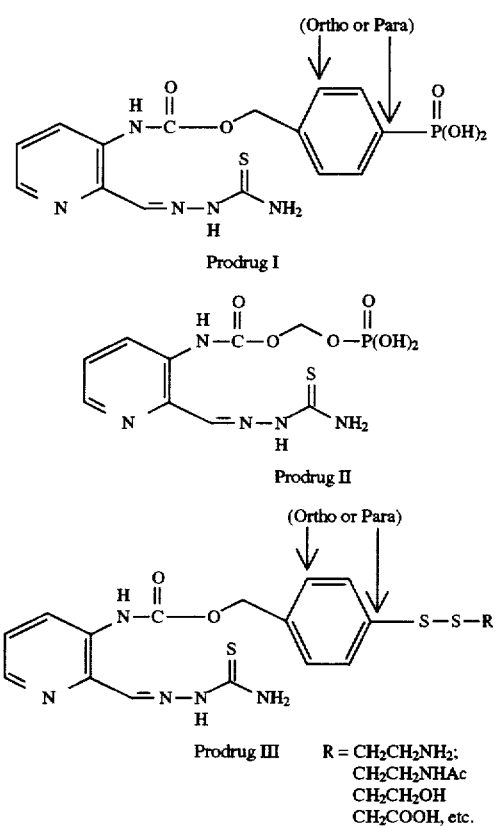

Prodrug I

Prodrug II

Prodrug III    R = CH$_2$CH$_2$NH$_2$;
CH$_2$CH$_2$NHAc
CH$_2$CH$_2$OH
CH$_2$COOH, etc.

The present invention relates to a compound according to the formula:

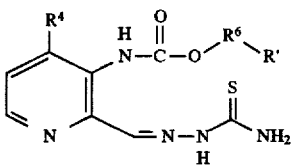

where

R$^4$ is H or CH$_3$ and

R$^5$ is CHR, benzyl or ortho or para substituted benzyl;

R is H, CH$_3$, CH$_2$CH$_3$, CH$_2$CH$_2$CH$_3$ or

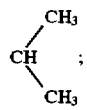

R' is a free acid phosphate, phosphate salt or an —S—S—R" group;

R" is CH$_2$CH$_2$NHR$^6$, CH$_2$CH$_2$OH, CH$_2$COOR$^7$, an ortho or para substituted C$_1$–C$_3$ alkylphenyl, or an ortho or para substituted nitro-phenyl;

R$^6$ is H, C$_1$–C$_4$ acyl group, trifluoroacetyl, benzoyl or substituted benzoyl group, and R$^7$ is H, C$_1$–C$_4$ alkyl, phenyl, substituted phenyl, or a benzyl or substituted benzyl.

The present invention also relates to pharmaceutical compositions which comprises an anti-neoplastic effective amount of any one or more of the prodrug compounds as set forth above in pharmaceutical dosage form. Optionally, and preferably, the pharmaceutical compositions according to the present invention also include a pharmaceutically acceptable additive, diluent or excipient and the preferred dosage form is an oral dosage form.

Therapeutic methods according to the present invention comprise administering to a patient suffering from cancer or having a tumor an anti-neoplasic effective amount of at least one or more of the prodrug compounds according to the present invention. In this aspect of the present invention, preferably the cancer will go into remission and, in the case of a tumor, the tumor will shrink substantially.

BRIEF DESCRIPTION OF THE FIGURES

FIG. 1 depicts the prodrugs of the present invention.

FIG. 9 depicts a graph of the conversion of Prodrug I (para) to 3-AP in the presence of liver S9 fraction.

FIGS. 10 and 11 depict a graph comparing the reduction in M109 tumor growth in Balb/c Mice treated with a control, 3-AP or Prodrug I (para).

DETAILED DESCRIPTION OF THE INVENTION

Figure 2:
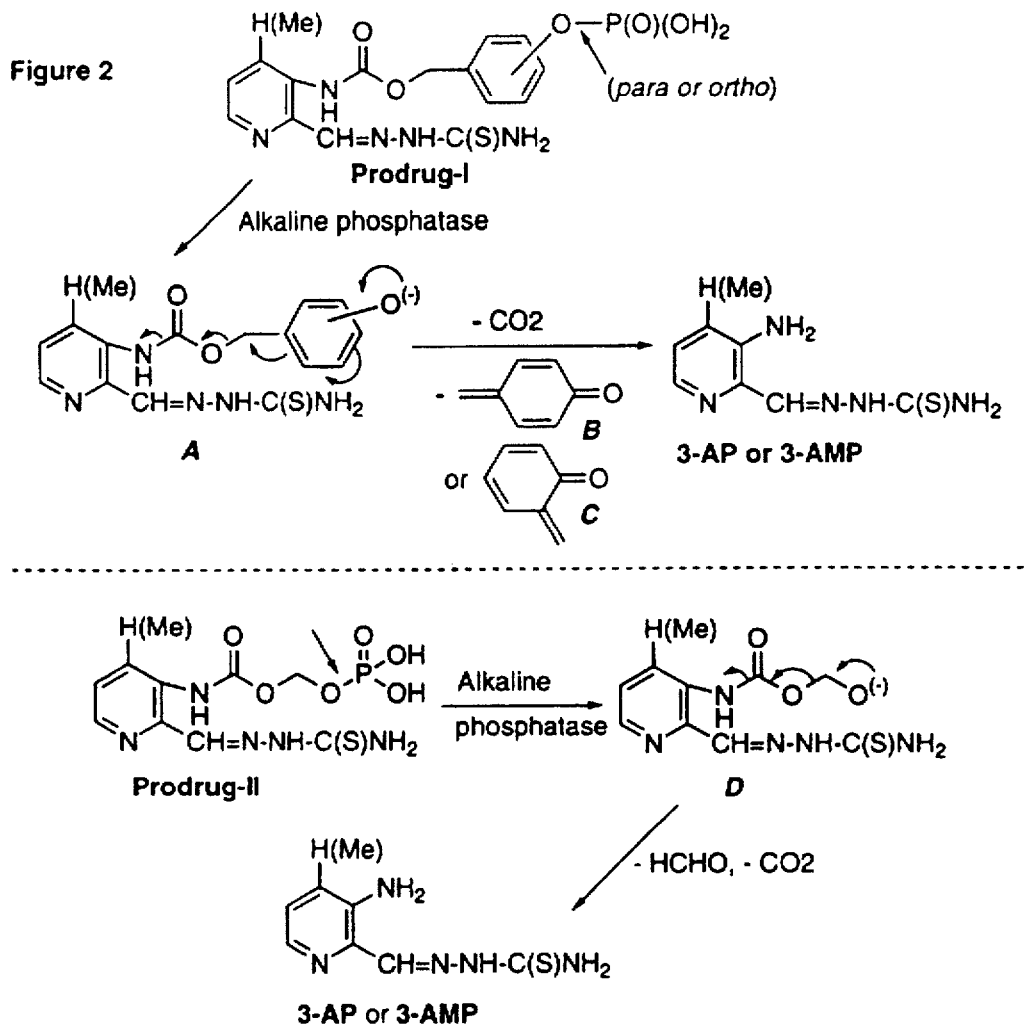
FIGS. 2 & 3 outline the intended drug releasing mechanism of the phosphate and disulfide containing prodrugs, respectively, in vitro and in vivo.

The term "patient" is used throughout the specification to describe an animal, including a mammal such as a human, to whom treatment with the compositions according to the present invention is provided. For treatment of those infections, conditions, or disease states which are specific for a specific animal such as a human patient, the term patient refers to that specific animal.

The term "neoplasia" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

The term "antineoplastic effective amount" is used throughout the specification to describe an amount of the present compounds which is used to treat a patient suffering from a cancerous tumor to prevent the further growth of the neoplasms, bring that growth under control and preferably, produce a remission of the tumor.

The term "therapeutically effective amount" is used throughout the specification to describe that amount of the compound according to the present invention which is administered to a mammalian patient, especially including a human patient, suffering from cancer, to reduce or inhibit the growth or spread of the hematogenous, ascitic or solid tumor. Preferably, the compounds according to the present invention will result in a remission of the malignant hematogenous, ascitic or solid tumor. In the case of solid tumors, the compounds according to the present invention will inhibit the further growth of the tumor tissue and preferably shrink the existing tumor.

The term "protected" is used to refer to a phosphate group or hydroxyl group in any one or more of the intermediates which is protected from undesired reactions, but which protection may be removed under selective conditions. Protection groups which may be used for this purpose include, for example, trichloroethyl, ethyl, cyanoethyl, trimethylsilylethyl, silylethyl, t-butyldimethylsilyl, t-butyl, triphenylsilyl and t-butyldiphenylsilyl, among numerous others. The blocking groups may be broadly chosen from the class of silyl blocking groups, ether blocking groups, ester blocking groups and related groups, each blocking group being chosen for its ability to protect a moiety from an undesirable reaction taking place and its ease of removal and compatibility of chemistry.

The present invention relates to prodrug forms of 3-aminopyridine-2-carboxaldehyde thiosemicarbazone (3-AP) and 3-amino-4-methylpyridine-2-carboxaldehyde thiosemicarbazone (3-AMP) which have increased water solubility, bioavailablity, and/or exhibit resistance to metabolic inactivation, in comparison to 3-AP and/or 3-AMP, respectively. To produce prodrug forms which are significantly more soluble than parent drugs 3-AP and 3-AMP, the 3-amino group of 3-AP or 3-AMP is derivatized with a methyl or urethane moiety, preferably urethane, which is substituted with an organophosphate group or a disulfide group as shown in FIG. 1. Prodrug compounds according to the present invention exhibit significantly greater water solubility and/or enhanced activity compared to the non-prodrug forms.

Synthesis of Prodrug Forms of 3-AP and 3-AMP
Synthesis of Prodrug I

Figure 4:
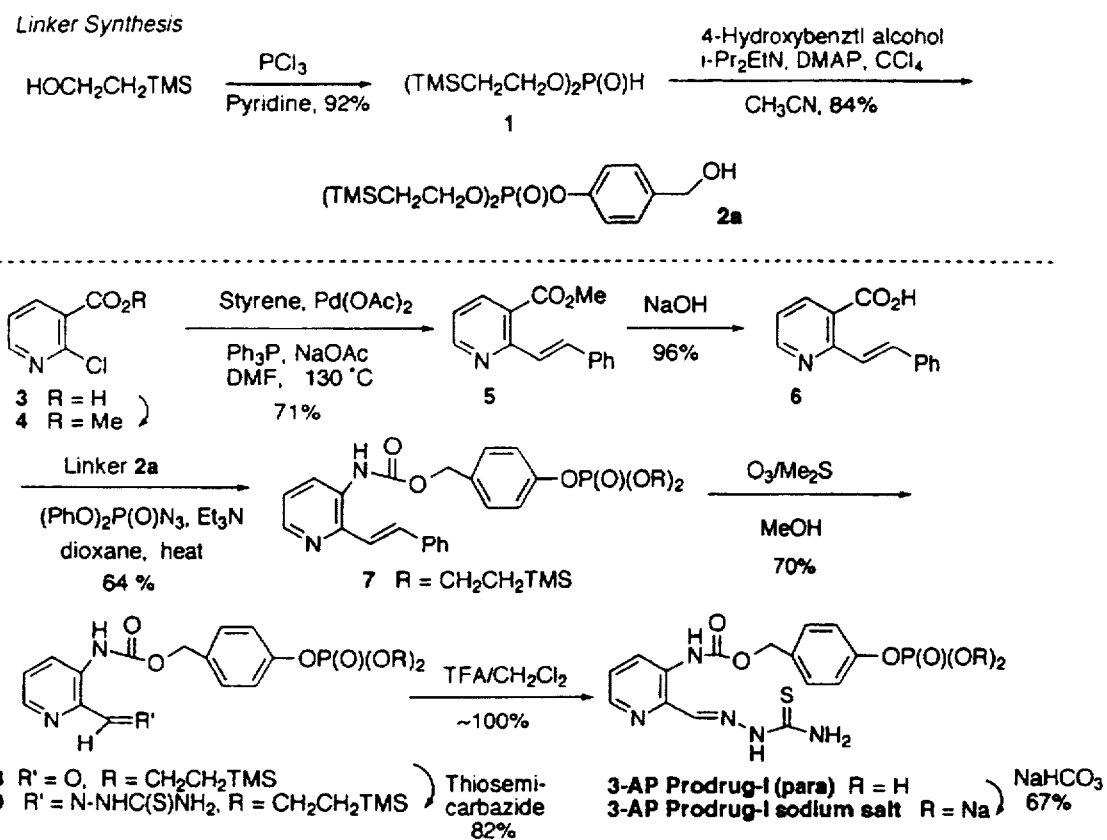
FIGS. 4 & 5. Schemes 4 and 5 provide a synthesis of prodrug I (both para and ortho).
Figure 5:
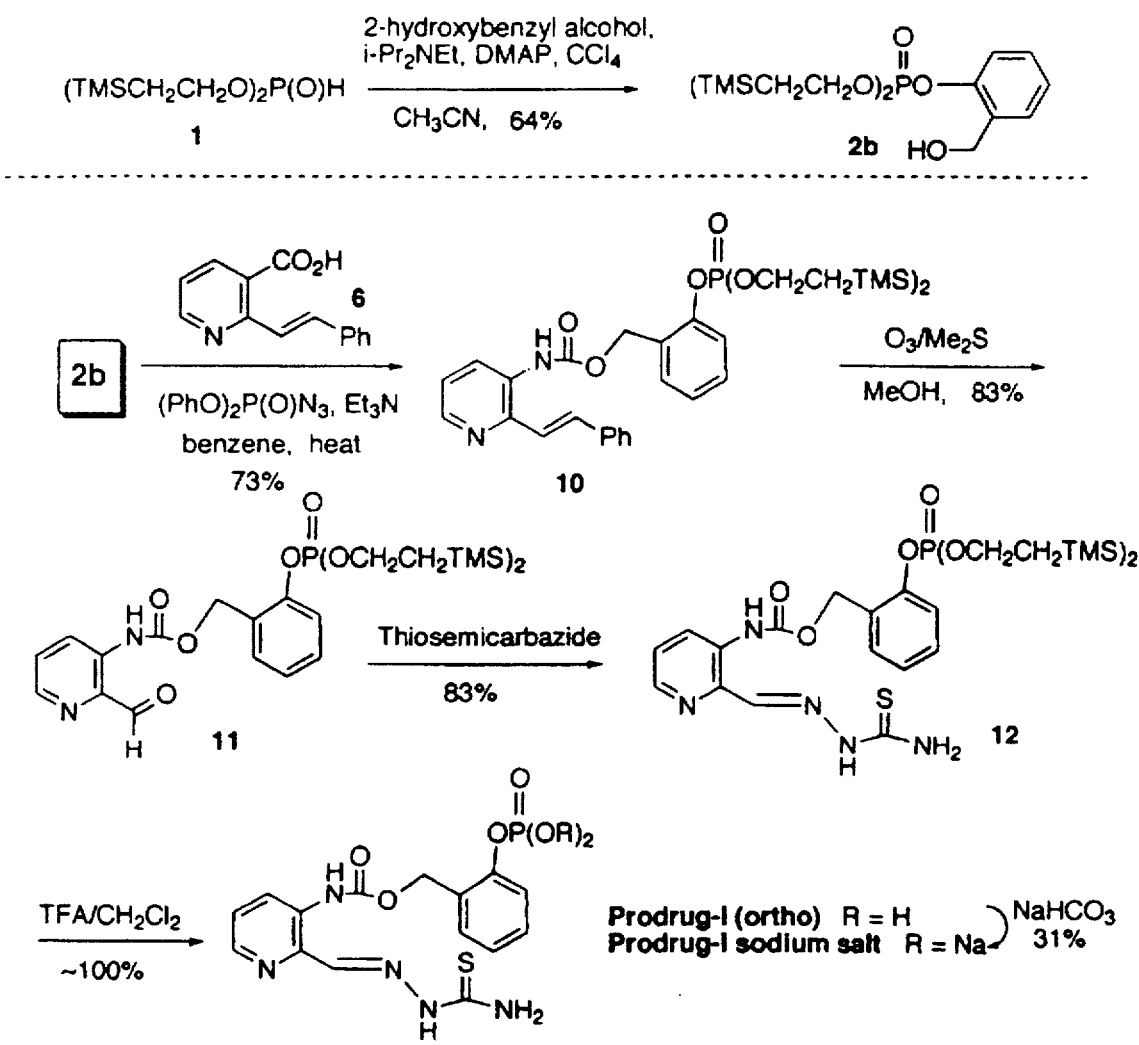

In the synthesis of prodrug I (para) according to the present invention, as set forth in FIG. 4, scheme 4, phosphate triester 2a is reacted with the 2-styrenyl-3-carboxylic acid pyridine analog 6 in the presence of (PhO)$_2$ P(O)N$_3$ and Et$_3$N to produce the phosphotriester urethane compound 7, which, after ozonolysis, followed by reaction with thiosemicabizide and removal of the phosphate ester protective groups produces prodrug I (para) of 3-AP. An analogous synthesis of prodrug I (ortho) is provided in FIG. 5, scheme 5, where the 2-vinylpyridine-3-carboxylic acid derivative 6 is condensed with phophate triester 2b to produce urethane compound 10 which is subsequently subjected to ozonolysis to produce the 3-urethane-pyridine-2-carboxaldehyde derivative 11, which is subjected to condensation with thiosemicarbazide to produce the thiosemicarbozone 12, which is subjected to acidic conditions (trifluroacetic acid in methylene chloride) to remove the trimethylsilyl ethyl phosphate blocking groups as depicted in FIG. 5 and produce prodrug I (para).

Synthesis of Prodrug II

Figure 6:
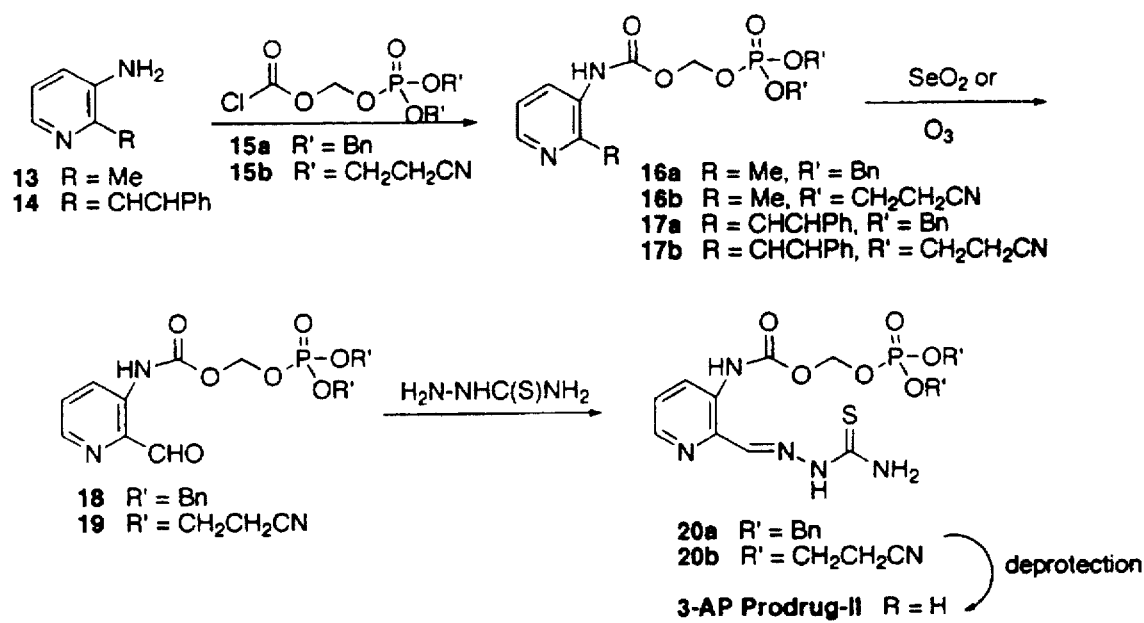
FIG. 6. Scheme 6 provides four alternative syntheses of prodrug II.

Synthetic schemes for the synthesis of Prodrug II is set forth in FIG. 6, scheme 6. Prodrug II is analogous to Prodrug I, except that the benzene ring in the urethane side chain of Prodrug I has been removed. As set forth in alternative scheme 6, in FIG. 6, Prodrug II is readily synthesized from standard precursors. In scheme 6, phosphotriester linker (15a–b) is reacted with 2-methylpyridine derivative 13 or 2-vinylpyridine derivative 14 (which may be prepared by a Stille vinylation of 2-chloro-3-amino pyridine, among other methods) to produce urethane derivatives 16 (a–b) and 17 (a–b), which are subsequently subjected to oxidation, for example, with ozone or selenium dioxide to form the 2-carboxaldehyde derivatives 18 and 19. Each of these 2-carboxaldehyde derivatives is then reacted with thiosemicarbazide, which reaction is followed by phosphotriester deprotection to produce prodrug II.

Synthesis of Prodrug III

Figure 7:
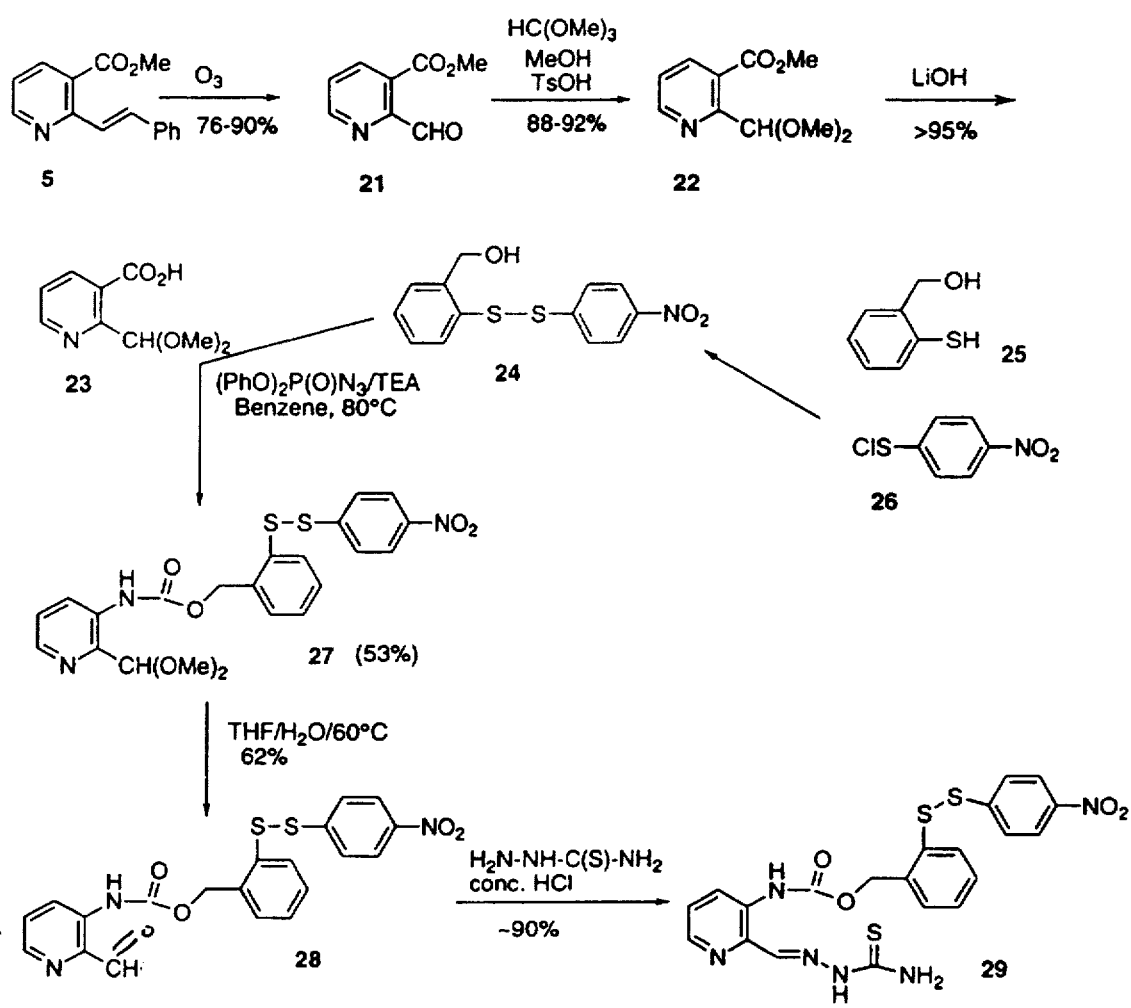
FIG. 7 outlines the synthesis of a disulfide prodrug 29.

The synthesis of prodrug III (ortho version, where R is a para nitrophenyl group) is depicted in FIG. 7, scheme 7. In this synthesis, vinyl derivative 5 (prepared according to the preparation set forth in FIG. 4, scheme 4) is subjected to ozonolysis to produce pyridine 2-carboxaldehyde 21, which is derivatized to the dimethyl acetal derivative 22 and then de-esterified to the acetal carboxylic acid derivative 23. Acetal carboxylic acid derivative 23 is reacted with disulfide intermediate 24 (prepared from the condensation of 2-thiolbenzyl alcohol 25 and p-nitrophenyl-chloromercaptide 26) in the presence of (PhO)$_2$P(O)N$_3$ in triethyamine and benzene to produce derivatized dimethyl acetal derivative 27 which is subsequently subjected to moderately elevated temperature and acidic conditions in water/THF to convert the acetal to the carboxaldehyde derivative 28. Carboxaldehyde 28 is subsequently reacted with thiosemicarbazide in the presence of a catalytic amount of concentrated HCl to produce prodrug 29 (ortho). The para version of prodrug 29 is synthesized by or in the same manner as is the ortho version with the exception that intermediate 24 is modified so that the benzylic alcohol group is in a position para to sulfur (by using para thiol benzyl alcohol) instead of ortho.

Figure 8:
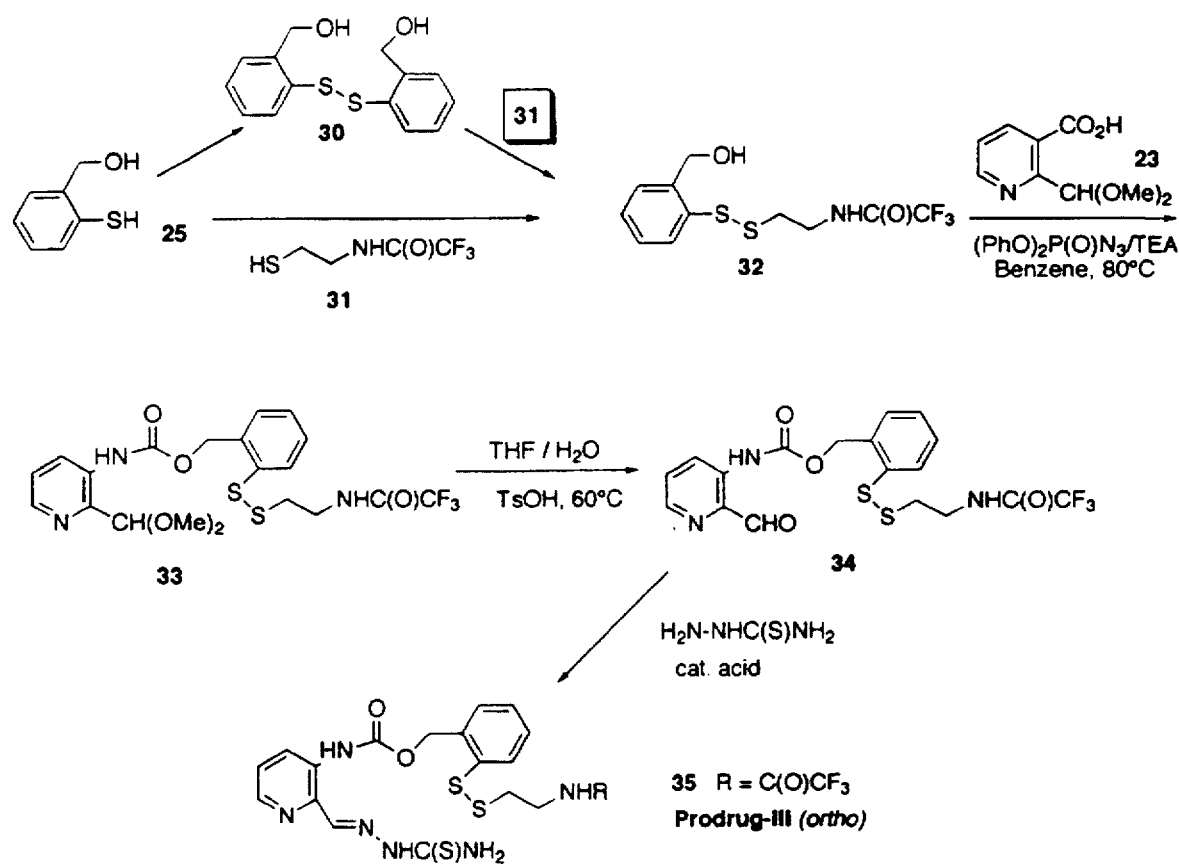
FIG. 8. Scheme 8, provides a synthesis of prodrug III.

FIG. 8 shows the synthesis of the ortho form of prodrug-III where R is a trifluoroacetyl group. Intermediate mixed disulfide 32 is produced by a trans-thiolation reaction with disulfide 30 which is produced by oxidation of ortho thiol benzyl alcohol and the trifluoroacetylatedamine alkylmercaptide 33. Mixed disulfide 32 is thereafter reacted with acetal carboxylic acid derivative 23 in the presence of (PhO)$_2$P(O)N$_3$ and triethylamine in benzene at 80° C. to produce urethane derivative 33 which is subsequently treated with toluenesulfonic acid in water and tetrahydrofuran at slightly elevated temperature (60° C.) to produce the carboxaldehyde derivative 34. Carboxaldehyde derivative 34 is then reacted with thiosemicarbazide in the presence of a catalytic amount of acid to produce prodrug III, where R is a trifluoroacetyl group.

Numerous other prodrug compounds according to the present invention as well as related, equivalent compounds may be readily synthesized by analogy by simply modifying the above-described synthetic pathways, utilizing methods which are well-known in the art.

Water Solubility

In order to test the water solubility of Prodrug I (disodium salt) compared to 3-AP, the following procedure was used. To test the water solubility of 3-AP in deionized water, 5 mg of 3-AP was placed in a 125 mL erlenmeyer flask to which was added 100 mL of water. The mixture was well shaken at room temperature. After 2 hours, the solid 3-AP was not totally dissolved in the water. Total water solubility of 3-AP in deionized water was <1 mg/20 mL. In the case of prodrug I (para), 8 mg of the prodrug was placed in a 50 mL erlenmeyer flask. 0.5 mL of water was added to the prodrug which readily dissolved to produce a clear light yellow solution after only a few minutes. Total water solubility of the prodrug (disodium salt) in deionized water was ≧16 mg/mL, a more than 300 fold increase in water solubility over 3-AP.

Bioactivation

The bioactivation of the phosphate containing prodrugs is envisioned to occur through cleavage of the phosphorous-oxygen bond which connects the phosphate group to the methyl or urethane moiety, followed by fragmentation with the loss of quinone methide, formaldehyde and/or $CO_2$, resulting in the parent drugs 3-AP or 3-AMP as end products. These pathways are depicted in FIG. 2. The quinone methides themselves can cause damage to DNA and thereby contribute to inhibition of cellular replication. Therefore, these quinone methides may act in an additive or synergistic manner to produce complimentary inhibition with the parent drugs.

Figure 3:
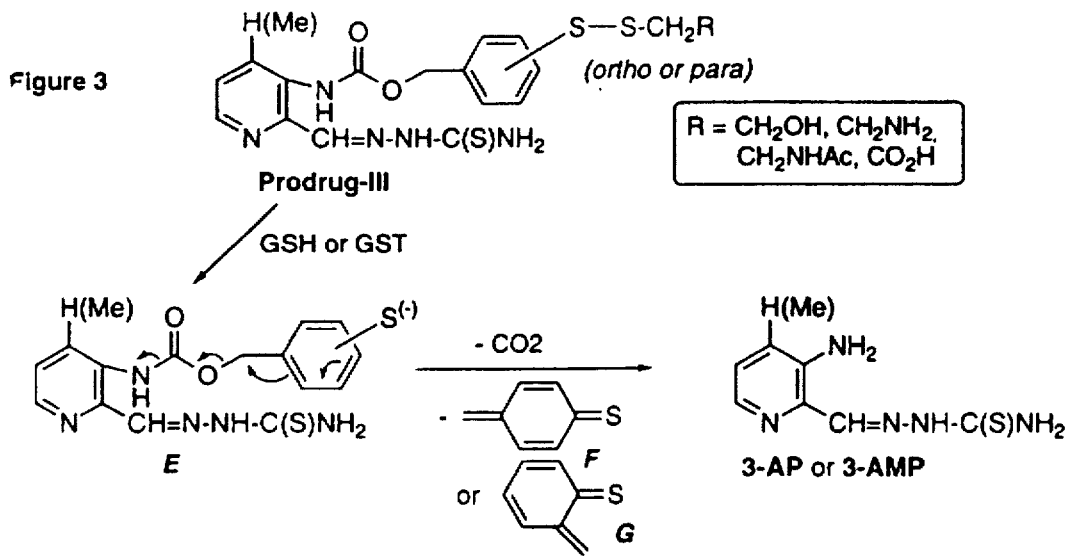

FIG. 3 outlines the intended pathway for the bioactivation of the disulfide linked prodrugs. While not being limited by way of theory or mechanism, it is believed that upon incubation with GSH or a related thiol, the reductive activation of the disulfide-linked prodrug takes place by a cascade of events wherein the sulfur substituent attached to the aromatic ring should serve as a leaving group (due to the electron withdrawing effects of the aromatic ring), followed by a similar fragmentation mechanism as with the phosphate containing prodrugs, resulting in the therapeutically effective agents 3-AP or 3-AMP and another quinone methide as end products.

FIG. 9 demonstrates the conversion of Prodrug I (para) to 3-AP in vitro in presence of an S9 fraction of rat liver. A 1 μM solution of Prodrug I in culture media was incubated with approximately 2.5 mg of liver S9 fraction. The prodrug concentration decreased very rapidly and was below detection limits after 100 minutes of incubation at 37° C. Approximately 80% of the prodrug was recovered as 3-AP and no other metabolites were found. The rate of conversion of Prodrug I to 3-AP was 20 nmole/min/mg rat liver tissue. The recovered 3-AP was stable in the liver S9 fraction. When Prodrug I was incubated in culture media alone at 37° C. for two hours, the prodrug concentration was relatively stable and no 3-AP was found by HPLC assay. This result indicates the release of 3-AP from Prodrug I to be an enzymatic process.

In vivo Efficacy

The results of an experiment comparing the in vivo efficacy of Prodrug I and 3-AP are shown in FIG. 10. Balb/c mice were subcutaneously injected in the right flank on Day 0 with 0.2 mL of a 5×10$^6$ cell/mL suspension of M109 tumor cells which had been grown to log phase in culture, trypsin digested to separate, washed with PBS and reconstituted. Injections of 3-AP, Prodrug I, or Vehicle Control were given to the rats twice on Day 3, once on Day 4, twice on Day 6 and once on Day 7. Ten mice received only injections of 3 AP, each injection providing a dose of 4.5 mg/kg body weight. Ten mice received only injections of Prodrug I, each injection providing a dose of 10 mg/kg body weight. Ten mice received only injections of the vehicle control. The size of the tumors were measured by palpation on Days 7, 10, 13 and 17, and these results are presented in FIG. 10. This experiment clearly shows that Prodrug I is slightly more effective in reducing tumor growth than an equal molar dose of 3-AP. FIG. 11 also compares the reduction in M109 tumor growth in Balb/c Mice using two vehicle controls (1-phosphate buffered serum and 2- 10% DMSO). These results also show that Prodrug I is more effective on a mole-to-mole basis than is 3-AP. Control I was used as a control for the prodrug; control 2 was used for the parent drug.

The therapeutic aspect according to the present invention relates to methods for treating neoplasia in animal or human patients, in particular tumors in humans comprising administering antineoplastic effective amounts of the prodrug compounds according to the present invention to inhibit further growth of the neoplasms, bring that growth under control and preferably, produce a remission of the tumor. In the method of the present invention, a therapeutically effective amount of at least one prodrug according to the present invention is administered to a patient suffering from cancer, or a malignant or non-malignant tumor to inhibit the growth or spread of such cancer or tumor. Preferably, in the therapeutic aspect of the present invention, a therapeutically effective amount will result in a remission of the cancer or hematogenous ascitic or solid tumor. Preferably, in the case of solid tumors, the tumor will actually shrink in size.

Pharmaceutical compositions based upon these prodrug compounds comprise the above described compounds in a therapeutically effective amount for treating neoplasia, optionally in combination with a pharmaceutically acceptable additive, carrier or excipient. One of ordinary skill in the art will recognize that a therapeutically effective amount will vary with the condition to be treated, its severity, the treatment regimen to be employed, the pharmacokinetics of the agent used, as well as the patient (animal or human) treated.

In general, it is preferable to administer the pharmaceutical composition in orally-administratable form, more preferably as enteric coated formulations such as tablets, capsules or the like, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the pharmaceutical compositions within the teachings of the specification to provide numerous formulations for a particular route of administration without rendering the compositions of the present invention unstable or compromising their therapeutic activity.

The present compounds are prodrug forms of the active anti-neoplastic agents 3-AP and 3-AMP. In certain pharmaceutical dosage forms, certain of the present compounds may be more appropriate than other compounds, depending upon the route of administration. One of ordinary skill in the art will recognize how to make use of the varied chemistry of the present compounds to provide one or more dosage forms to facilitate delivery of active compounds to a targeted site within the patient. The individual of ordinary skill also will take advantage of favorable pharmacokinetic parameters of the prodrug forms, where applicable, in delivering the present compounds to a targeted site within the patient to maximize the intended antineoplastic effect of the compound.

The amount of compound included within the therapeutically active formulations according to the present invention is an effective amount for treating the cancer or malignant tumor. In general, a therapeutically effective amount of the compound according to the present invention in dosage form usually ranges from less than about 0.05 mg/kg to about 500 mg/kg of body weight of the patient to be treated, or considerably more, depending upon the compound used, the tumor type to be treated, the ability of the active compound to localize in the tissue to be treated, the route of administration and the pharmacokinetics of the compound in the patient. In the case of treating solid tumors, the compound is preferably administered in amounts ranging from about 0.05 mg/kg to about 250 mg/kg or more at one time. This dosage range generally produces effective blood level concentrations of active compound ranging from about 0.01 to about 500 micrograms per ml of blood in the patient to be treated. The duration of treatment may be for one or more days or may last for several months or considerably longer (years) depending upon the disease state treated. It is noted that the use of a prodrug compound according to the present invention will, in preferred instances, allow less (on a molar basis) prodrug compound to be administered to a patient to provide an intended result compared to 3-AP or 3-AMP. Thus, the present compounds and methods are also advantageous inasmuch as they are believed to be significantly less toxic to patients than are 3-AP and 3-AMP, because an intended anti-cancer benefit may be realized in a patient with less compound (on a molar basis).

In the therapeutic aspect of the present invention, administration of the active compound may range from continuous (intravenous drip) to intramuscular, to several oral administrations per day (for example, Q.I.D.) and may include parenteral, including intravenous and intramuscular, oral, topical, subcutaneous, transdermal (which may include a penetration enhancement agent), buccal and suppository administration, among other routes of administration. Oral administration is the preferred route of administration of the present compounds.

To prepare the pharmaceutical compositions according to the present invention, a therapeutically effective amount of one or more of the compounds according to the present invention is preferably intimately admixed with an optional pharmaceutically acceptable carrier according to conventional pharmaceutical compounding techniques to produce a dose. A carrier may take a wide variety of forms depending on the form of preparation desired for administration, e.g., oral or parenteral.

For parenteral formulations, the carrier may comprise sterile water or aqueous sodium chloride solution in combination with other ingredients which aid dispersion, such as ethanol and other pharmaceutically acceptable solvents, including DMSO, among others. Of course, where solutions are to be used and maintained as sterile, the compositions and carrier must also be sterilized. Injectable suspensions may also be prepared, in which case appropriate liquid carriers, suspending agents and the like may be employed.

In preparing preferred pharmaceutical compositions in oral dosage form, any one or more of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The compounds and compositions according to the present invention are used to treat cancer in mammals, including humans. Generally, to treat malignant tumors, the compositions will be administered in parenteral, preferably intravenous dosage form in amounts ranging from about 10 micrograms up to about 500 mg or more one to four times per day. The present compounds are preferably administered orally, but they also may be administered in an alternative manner, for example, parenterally or even topically or in suppository form.

Compounds according to the present invention may be administered alone or in combination with other agents, especially including other compounds of the present invention. In addition, the administration of one or more compounds according to the present invention with other antineoplastic agents, in combination chemotherapy, such as antimetabolites, etoposide, doxorubicin, taxol, vincristine, cyclophosphamide or mitomycin C, among numerous others, is contemplated by the present invention.

The present invention is now described, purely by way of illustration, in the following examples. It will be understood by one of ordinary skill in the art that these examples are in no way limiting and that variations of detail can be made without departing from the spirit and scope of the present invention.

EXAMPLES

The detailed reaction conditions and characterizations of each compound in the following procedures are provided in this section. All NMR spectra were measured at 300 MHZ for 1 H and at 75 MHZ for 13 C on QE Plus 300 MHZ NMR spectrometer. MS spectra were recorded on VG ZAB-SE mass spectrometer and a VG 70-SE-4F instrument. Some relevant references are also included herein. All solvents were distilled prior to use.

Synthesis of Prodrug I
Synthesis of Phosphate Triester Compound 2a

To a solution of 4-hydroxybenzyl alcohol (1.09 g, 8.79 mmol) in 30 ml of dry acetonitrile at 0 °C. was added carbon tetrachloride (6.76 g, 44 mmol), N,N-diisopropylethylamine (2.39 g, 18.5 mmol) and DMAP (107 mf, 0.88 mmol). After 2 minutes, di-(2-(trimethylsilyl) ethyl phosphite 1 in 5 ml of acetonitrile was added dropwise. The reaction was slowly warmed to room temperature over 4 h. The solvent was removed and residue was flash chromatographed (hexane: EtOAc, 1: 1) to give 2a as a colorless oil. $^1$H NMR (CDCl$_3$, 300 MHZ) δ 7.34 (ABq, J=8.4 Hz, 2H), δ 7.21 (ABq, J=8.7 Hz, δ 4.67 (s, 2H), δ 4.18–4.30 (m, 4H), δ 1.04–1.18 (m, 4H), δ 0.03 (s, 18H).

Synthesis of 2-Chloronicotinic Methyl Ester Compound 4

To a suspension of 2-chloronicotinic acid 3 (15.8 g, 0.1 mol) in 100 ml of dry MeOH at 0° C. was added thionyl chloride (17.8 g, 0.15 mol) dropwise. The reaction was then slowly warmed to room temperature and stirred for 2 days. The solvent was then removed via vacuum and the residue was dissolved in sat. NaHCO3. The resulted basic solution was then extracted with EtOAc (3×100 ml). The combined organic phases were washed with brine, dried with NaSO4, concentrated via vacuum to give 2-chloronicotinic methyl ester 4(15.3 g, 89%) as an oil: $^1$H NMR (CDCl$_3$, 300 MHZ) δ 8.52 (dd, J=1.8, 4.5 Hz, 1H), δ 8.19 (dd, J=2.1, 7.8 Hz, 1H), δ 7.38 (dd, J=4.8, 7.8 Hz, 1H), δ 3.97 (s, 3H)

Synthesis of Vinyl Ester Pyridine Compound 5

To a solution of 2-chloronicotinic methyl ester 4 (1.71 g, 10 mmol) in 10 ml of DMF was added sodium acetate (1.64 g, 20 mmol), triphenylphosphine (1.05 g, 4, mmol), palladium(II) acetate (0.1 12g, 0.5 mmol) and followed by addition of styrene (10.4 g, 0.10 mol). The resulted mixture was heated to 130 ° C. for 3 days. The reaction was cooled to room temperature and quenched with 20 ml of water. The mixture was extracted with EtOAc (3×50 ml). The organic phases were dried over sodium sulfate and concentrated in vacuum. The residue was flash chromatographed (hexane: EtOAc, 8:1 to 6: 1) to give 5 (1.70 g, 71%) as a yellow oil: $^1$H NMR (CDCl$_3$, 300 MHZ) δ 8.73 (dd, J=1.4, 4.5 Hz, 1H, δ 8.21 (dd, J=1.8, 7.8 Hz, 1H), δ 8.15 (ABq, J=15.6 Hz, 1H), δ 7.65 (ABq, J=7.2 Hz, 2H) δ 7.37 (ABq, J=7.5 Hz, 2H), δ 7.30–7.42 (m, 1H), δ 7.23 (dd, J=4.8, 7.8 Hz, 1H), δ 3.97 (s, 3H)

Synthesis of Vinyl Carboxylic Acid Compound 6

To a solution of vinyl ester pyridine compound 5 (3.31 g, 13.85 mmol) in 10 ml of THF was added NaOH (3N, 5 ml) and the reaction was stirred overnight. The reaction solution was then acidified to pH 7 with Dowex 50w8-100. The resin was filtered off and the filtrate was concentrated to give crude 6 (3. 0 g, 96%) which is suitable for the next step reaction.

$^1$H NMR(acetone-$d_6$, 300 MHZ) δ 8.52 (ABq, J=15.9 Hz, 1H), δ 8.45 (dd, J=1.5, 4.5 Hz, 1H).), δ 8.20 (dd, J=1.5, 7.5 Hz, 1H), δ 7.82 (ABq, J=15.9 Hz, 1H), δ 7.59 (7.58, J=1.5 Hz, 1H), δ 7.56 (s, 1H), δ 7.15–7.30 (m, 3H), δ 7.04 (dd, J =4.5, 7.8 Hz, 1H)

Synthesis of Urethane Compound 7

A mixture of 6 prepared above (1.0 g, 4.46 mmol), diphenyl phosphoryl azide (1.3 g, 2.97 mmol) and triethylamine (0.48 g, 4.75 IT mol) in 10 ml of benzene was heated to reflux for 10 min. Alcohol 2a (1.2 g, 2.97 mmol) in 5 ml of benzene was added and the mixture was heated at reflux for 3 h. 5 ml of dioxane was added and the mixture was continually heated for 2 h. After cooling, the solvent was removed and the residue was purified by silica gel column (hexane: EtOAc, 5:1 to 2:1) to yellow solid 7 (1.20 g, 64%):
$^1$H NMR (CDCl$_3$, 300 MHZ) δ 8.41 (dd, J=1.2, 5.1 Hz, 1H), δ 7.74 (d, J=15.9 Hz, 1H), δ 7.57 (d, J=8.1 Hz, 2H), δ 7.15–7.45 (m, 10H), δ 6.77 (br, 1H), δ 5.20 (s, 2H), δ 4.20–4.32 (m4H,) δ 1.05–1.20 (m, 4H), δ 0.03 (s, 18H)

Synthesis of 2-Carboxaldehyde Urethane Compound 8

A solution of 7 (1.14 g, 1.82 mmol) in CH$_2$Cl$_2$/MeOH (100 ml, 1:4) was ozonized at –78° C. and the reaction was monitored by TLC. After the reaction, the excess ozone was removed by bubbling the reaction mixture with oxygen until the blue reaction solution became colorless. The reaction was then quenched with methyl sulfide (3 ml) at –78° C. and solution was allowed to slowly warmed up and stirred at room temperature for 5 h. The solvent was evaporated, and the residue was purified by silica gel chromatography (hexane: EtOAc, 4:1) to afford 8 (0.708 g, 70%) as a light yellow oil: $^1$H NMR (CDCl$_3$, 300 MHZ) δ 10.48 (br, 1H), δ 10.07 (s, 1H), δ 8.83 (d, J=8.7 Hz, 1H), δ 8.44 (dd, J=0.9, 4.2 Hz, 1H), δ 7.49 (dd, J=4.5, 8.7 Hz, 1H), δ 7.40 (ABq, J=8.4 Hz, 2H), δ 7.23 (ABq, J=8.1 Hz, 2H, δ 5.19 (s, 2H), δ 4.18–4.28 (m, 4H), δ 1.02–1.20 (m, 4H), δ 0.02 (s, 18H)

Synthesis of Thiosemicarbazone Compound 9

To a solution of aldehyde 8 (1.40 g, 2.54 mmol) in EtOH/H$_2$0 (6 ml, 5:1) was added solution of thiosemicarbazide (0.254 g, 2.79 mmol) in EtOH/H2O (30 ml, 7:3) drop After stirring at room temperature for 3 h, the mixture was filtered and solid was rinsed with 5 ml of EtOH/H$_2$O (7:3) and 5 ml of ether to afford 9 (1.20 g) as a white solid. The filtrate was concentrated and the residue was purified by silica gel chromatography (CH$_2$Cl$_2$:MeOH=20:1) to afford 9 (0.096 g). The combined yield was 1.296 g (82%).

$^1$HNMR (CD30D, 300 MHZ) δ 8.25–8.32 (m, 2H), δ 8.19 (s, 1H), δ 7.46 (ABq, J=8.7 Hz, 2H), δ 7.41 (dd, J=48, 8.4 Hz, 1H), δ 7.23 (ABq, J=8.1 Hz, 2H), δ 5.21 (s, 2H), δ 4.20–4.40 (m, 4H), δ 1.02–1.20 (m, 4H), δ 0.03 (s, 18H)

Synthesis of Prodrug I (para)

Free Acid: Compound 9 (48 mg, 0.077 mmol) was treated with CH$_2$Cl$_2$/TFA (1 ml, 4:1) at room temperature for 30 min. The solvent was then removed in vacuum and the residue was washed with CH$_2$Cl$_2$/MeOH (5 ml, 10:1) to offer the free acid form of Prodrug I (free acid) as a yellow solid (35 mg, 108%). $^1$H NMR (DMSO-$d_6$, 300 MHZ) δ 11.75 (s, 1H), 9.97 (br, 1H), 8.53 (br, 1H), 8.39 (d, J=4.2 Hz, 1H), 8.30 (d, J=8.1 Hz, 1H), 8.23 (s, 1H), 7.94 (br, 1H), 7.45 (dd, J=3.6, 4.8 Hz, 1H), 7.39, (ABq, J=8.4 Hz, 2H) 7.18 (ABq J=7.8 Hz, 2H), 5.13 (s, 2H).

Sodium Salt: Compound 9 (47 mg, 0.075 mmol) was treated with ° CH$_2$Cl$_2$/TFA (1 ml, 4:1) at room temperature for 30 min. The solvent was then removed in vacuum and the crude acid of Prodrug I was dissolved in 2.5 ml of 0.5 M NaHCO$_3$. The resulted solution was purified by a C-18 column to give the sodium salt form of Prodrug I (22 mg, 67%). $^1$H NMR (CD$_3$0D, 300 MHZ) δ 8.30–8.42(m, 2H), 8.19(s, 1H), 7.39 (dd, J=4.5, 8.4 Hz, 1H), 7.28, (ABq, J=9.3, 10.5 Hz, 4H), 5.12 (s, 2H).

Synthesis of Prodrug I (ortho)
Synthesis of Phosphotriester Intermediate 2b

To a solution of 2-hydroxybenzyl alcohol (1.19 g, 9.57 mmol) in 30 ml of dry acetonitrile at 0° C. was added carbon tetrachloride (7.37 g, 47.8 mmol), N,N-diisopropylethylamine (2.60 g, 20.1 mmol) and DMAP (117 mg, 0.96 mmol). After 2 minute, di-(2-(trimethylsilyl)ethyl phosphite(2.70 g, 9.57 mmol) in 5 ml of acetonitrile was added dropwise. The reaction was slowly warmed to room temperature overnight. The solvent was removed and residue was flash chromatographed (hexane:EtOAc, 4:1) to give 2b (2.50 g, 64%) as a colorless oil. $^1$HNMR (CDCl$_3$, 300 MHz) δ 7.44 (d, J=8.4 Hz, 1H), δ 7.15 , 7.35 (m, 3H), δ 4.64 (s, 2H), δ 4.18–4.35 (m, 4H), δ 4.09 (br, 1H0, 1/13 (dd, J=6.3, 10.2, 4H), δ 0.35 (s, 18H)

Synthesis of urethane compound 10

A mixture of 6 (2.0 g, 8.91 mmol), diphenyl phosphoryl azide (2.61 g, 9.50 mmol) and triethylamine (0.96 g, 9.50 mmol) in 20 ml of benzene was heated to reflux for 10 min. Alcohol 2b (2.40 g, 5.94 mmol) in 5 ml of benzene was added and the mixture was heated to reflux for 4 h. After cooling, the solvent was removed and the residue was purified by silica gel column (hexane:EtOAc, 4:1) to yellow solid 10 (2.41 g, 73%): $^1$H NMR (CDCl$_3$, 300 MHz) δ 8.38 (d, J=4.5 Hz, 1H), δ 8.19 (d,br, J=6.9 Hz, 1H), δ 7.74 (d, J=15.3 Hz, 1H), δ 7.63 (d, J=7.2 Hz, 2H), δ 7.10–7.50 (m, 10H), δ 5.32 (s, 2H), δ 420–4.38 (m, 4H), δ 1.05–1.20 (m, 4H), δ 0.04 (s, 18H)

Synthesis of Carboxaldehyde Urethane Compound 11

A solution of 10 (2.30 g, 3.70 mmol) in CH$_2$Cl$_2$/MeOH (50 ml, 1:4) was ozonized at –78° C. and the reaction was monitored by TLC. After the reaction, the excess ozone was removed by bubbling the reaction mixture with oxygen until the blue reaction solution became colorless. The reaction was then quenched with methyl sulfide (3 ml) at –78° C. and the solution was allowed to slowly warmed up and stirred at room temperature for 5 h. The solvent was evaporated, and the residue was purified by silica gel chromatography (hexane:EtOAc, 4:1) to offer 11 (1.70 g, 83%) as light yellow oil: $^1$H NMR (CDCl$_3$, 300 MHz) δ 10.48 (br, 1H), δ 10.50(s, 1H), δ 10.05 (s, 1H), δ 8.86 (d, J=8.7 Hz, 1H), δ 8.45 (dd, J=1.5, 4.2 Hz, 1H), δ 7.4–7.55 (m, 3H), δ 7.35 (tdJ=1.5, 7.5 Hz, H), δ 7.20 (t, J=7.5 Hz, 2H), δ 5.35 (s, 2H), δ 4.18–4.28 (m, 4H), δ 1.02–1.20 (m, 4H), δ 0.02 (s, 18H)

Synthesis of Thiosemicarbazone Compound 12

To a solution of aldehyde 11 (1.60 g, 2.90 mmol) in EtOH/H$_2$O (5 ml, 7:3) was added solution of thiosemicarbazide (0.29 g, 3.19 mmol) in EtOH/H$_2$O (50 ml, 7:3) at rt. After stirring at room temperature for 4 h, the mixture was filtered and solid was rinsed with 5 ml of EtOH/H$_2$O (7:3) and 5 ml of ether to afford 12 (1.50 g, 83%) as yellow solid. $^1$H NMR (DMSO-d6, 300 MHz) δ 11.73 (s, 1H), δ 10.02(br, 1H), δ 8.48 (br, 1H), δ 8.20–8.55 (m, 3H), δ 7.89 (br, 1H), δ 7.10–7.60 (m, 5H), δ 5.23 (s, 2H), δ 4.00–4.30 (m, 4H), δ 0.9–1.20 (m, 4H), δ0.03 (s, 18H)

Free Acid: Synthesis of Prodrug I (ortho)

Compound 12 (580 mg, 0.93 mmol) was treated with CH$_2$Cl$_2$/TFA (1 ml, 4:1) at room temperature for 1 h. The solvent was then removed in vacuum to offer free acid Prodrug-I (ortho) as yellow solid (395 mg, 102%). $^1$H NMR (DMSO-d6, 300 MHz) δ 11.89 (s, 1H), 10.16 (br, 1H), 8.57 (br, 1H), 8.48 (d, J=7.1 Hz, IH), 8.40 (d, J=8.4 Hz, 1H), 8.23 (s, 1H), 8.12 (br, 1H), 7.60 (dd, J=5.1, 8.4 Hz, 1H), 7.46, (d, J=8.4 Hz, 1H), 7.27–7.38, (m, 2H), 7.20 (t, J=7.2Hz, 2H), 51.25 (s, 2H)

Sodium Salt:

The crude acid Prodrug-I (ortho) was dissolved in 50 ml of sat. NaHCO$_3$. The resulted solution was purified by a C-18 column to give sodium salt of Prodrug-I (ortho) (120 mg, 31%). $^1$HNMR (CD$_3$OD, 300 MHz) 8.44 (br, 1H), δ 8.29 (d, J=3.9 Hz 1H), 8.24(s, 1H0, 7.37 (dd, J=4.8, 8.4 Hz, 1H), 7.25–7.35, (m, 1H),), 7.20 (td, J=1.5, 7.5 Hz, 1H), ), 6.89 (t, J=7.5 Hz, 1H), 5.37 (s, 2H)

Synthesis of Pyridine Carboxaldehyde 21

A methanol (140 mL) and dichloromethane (55 mL) solution of 5 (10.0 g, 41.84 mmol) was subjected to ozonalysis at −78° C. for 1 hr. The greenish solution was then quenched with dimethylsulfide (10 mL) at −78 ° C. The reaction mixture was allowed to stirred at rt overnight. The solvent was removed in vacuo to give a residue, which was purified on silica gel to provide 6.24 g (90%) of the aldehyde 21 as a off-white solid. $^1$ H NMR of 21 (CDCl$_3$): δ 10.35 (s, 1H), 8.89–8.91 (m, 1H), 8.10–8.13 (m, 1H), 7.57–7.61 (m, 1H), 4.00 (s, 3H).

Synthesis of Pyridine Dimethylacetal Methyl Ester 22

To a methanol solution (47 mL) of aldehyde 21 (3.10 g, 18.79 mmol) was added trimethylorthoformate (10.3 mL, 93.95 mmol) along with a catalytic amount of TsOH. The reaction was heated to reflux for 12 hr. The reaction mixture was cooled and the solvent was evaporated to give a residue, which was redissolved in EtOAc (125 mL) and Et$_2$O (25 mL). The resulting organic layer was washed with saturated sodium bicarbonate solution and brine. The organic layer was dried (Na$_2$SO$_4$) and conc. in vacuo to provide 3.65 g (92%) of the dimethylacetal 22 as a thick oil.

$^1$H NMR of 22 (CDCl$_3$): δ 8.63–8.64 (m, 1H), 7.93–7.96 (m, 1H), 7.20–7.24 (m, 1H), 5.96 (s, 1H), 3.80 (d, J=1.0 Hz, 3H), 3.31 (s, 6H).

Synthesis of Pyridine Dimethyl Acetal Carboxylic Acid 23

To a THF (10 mL) solution of 22 (3.65 g, 17.29 mmol) was added a 3N NaOH solution (8.64 mL, 25.93 mmol) at rt. The yellownish solution was stirred at rt for 22 hr. The reaction was acidified with Dowex acidic resin (50WX8-100) to pH=4.5. The solids were filtered and rinsed with THF (30 mL). The filtrates were conc. in vacuo to provide 3.4 g (100%) of the crude acid 23 as pale yellow foam. $^1$H NMR of 23 (DMSO-d$_6$): δ 8.42–8.44 (m, 1H), 7.90–7.93 (m, 1H), 7.24–7.28 (m, 1H), 6.26 (s, 1H), 3.27 (s, 6H).

Synthesis of Urethane Disulfide Compounds 27

A benzene suspension (30 mL) of the crude acid 23 (894 mg, 4.54 mmol), disulfide linker 24 (1.33 g, 80% pure, 4.54 mmol), triethylamine (0.63 mL, 4.54 mmol) and diphenyl phosphorylazide (0.98 mL, 4.54 mmol) was heated to reflux for 16 hr. The reaction was cooled to rt, and the solvent was removed in vacuo (under 40 ° C.) to give a residue, which was purified by silica gel chromatography (40–60% EtOAc/hexanes) to provide 0.942 g (53%) of 27.

$^1$H NMR of 27 (CDCl$_3$): δ 8.60–8.48 (m, 2H), 8.14–8.23 (m, 3H), 7.25–7.67 (m, 7H), 5.41 (s, 2H), 5.33 (s, 1H), 3.46 (s, 6H).

Synthesis of Urethane Disulfide Carboxaldehyde Compound 28

To a THF (20 mL) solution of 27 (700 mg, 1.437 mmol) was added water (3 mL) and a catalytic amount of TsOH. The resulting solution was heated at 60° C. for 16 hr. The reaction was allowed to cool to rt, and the solvent was removed in vacuo. The resulting residue was purified by silica gel chromatography (30–40% EtOAc/hexanes) to afford 391 mg (62%) of 28 as yellow powder.

$^1$H NMR of 28 (CDCl$_3$): δ 10.57 (s, 1H), 10.09 (s, 1H), 8.85 (d, J=8.7 Hz, 1H), 8.46 (d, J=4.4Hz, IH, 8.19–8.16 (m, 2H), 7.69–7.31 (m, 7H), 5.45 (s, 2H).

Synthesis of Prodrug 29 (ortho)

To a THF (6 mL) solution of 28 (175 mg, 0.397 mmol) was added a warm (~40° C.) aqueous (0.75 L) solution of thiosemicarbazide (18.2 mg, 0.197 mmol). To the resulting yellow solution was added 2 drops of 10% Hcl. The reaction was stirred at rt for 3 hr. The solvent was removed in vacuo, and the product was coevaporated with THF (4×5 mL). The yellownish solids thus obtained were dried under high vacuum for 12 hr to provide the desired disulfide prodrug 29 in nearly 100% yield.

$^1$H NMR of 29 (DMSO-d$_6$): δ 11.68 (s, 1H), 9.98 (bs, 1H), 8.40–8.35 (m, 2H), 8.23–8.19 (m, 2H), 7.90–7.35 (m, 9H), 5.36 (s, 1H), 5.25 (s, 1H).

Synthesis of Disulfide Intermediate 32

To a mixture of 2-thiobenzyl alcohol 25 (2.63 g, 18.78 mmol), 2-thioethyl trifloroacetamide 31 (3.25 g, 18.78 mmol), and triethylamine (2.85 g, 28.2 :mmol) in 50 ml of THF/H2O (50 ml, 4:1) at 0 ° C. was added hydrogen peroxide (1.7 ml, 30% w/w) dropwise. The reaction was stirred at 0 ° C. for 30 min and then acidified with conc. Hcl to pH 2. The mixture was extracted with EtOAc, 1:1) to give mixture of 32 and thioethyl trifloroacetamide dimer (3.93 g). The mixture can be used for next step without further purification. A small portion of pure 32 was also obtained as a colorless oil.

$^1$H NMR (CDCl$_3$, 300 MHz) δ 7.70–7.82 (m, 1H), δ 7.47–7.53 (m, 1H), δ 7.30–7.40 (m, 2H), δ 6.69(br, 1H), δ 4.88(s, 2H), δ 3.67 (q, J=6.3, 2H), δ 2.89 (t, J=6.3, 2H), δ 2.16 (br, 1H).

Synthesis of Urethane Disulfide Dimethylacetal 33

A mixture of crude 23 (1.38 g, 7.0 mmol), crude 32 (3.5 g, 11.3 mmol), diphenyl phosphoryl azide (3.09 g, 11.3 mmol) and triethylamine (1.14 g, 11.3 mmol) in 25 ml of benzene was heated to reflux for 12 h. After cooling, the reaction mixture was directly loaded on the silica column and eluted with solvent (hexane:EtOAc, 2:1) to give pale yellow oil 33 (1.50 g, 42%):

$^1$H NMR (CDCl$_3$, 300 MHz) δ 8.48 (s, 1H), δ 8.46 (s, 1H), δ 8.23 (dd, J=0.9, 4.5 Hz, 1H), δ 7.81 (dd, J=1.5, 6.0 Hz, 1H), δ 7.20–7.50 (m, 3H), δ 6.87 (br, 1H), δ 5.41 (s, 2H), δ 5.33 (s, 1H), δ 3.60–3.72 (m, 2H), δ 3.47 (s, 6H), δ 2.89 (t, J=6.6, 2H).

Synthesis of Urethane Disulfide Carboxaldehyde Compound 34

A solution of 33 (0.394 g, 0.78 mmol) and catalytic amount of PTSSA in THF/H20 (4 ml/ml) was heated to 60 ° C. and the reaction was monitored by TLC. After 30 h, the solvent was evaporated, and the residue was purified by silica gel chromatography (hexane:EtOAc, 2:1) to offer 34 (0.282 g, 79%) as a light yellow solid:

$^1$H NMR (CDCl$_3$, 300 MHz) δ 10.55 (s, 1H), δ 10.08 (s, 1H), δ 8.80 (d, J=8.4 Hz, 1H), δ 8.47 (d, J=8.4 Hz, 1H), δ 8.47 (d, J=4.2 Hz, 1H), δ 7.83 (d, J=7.5Hz, 1H), δ 7.30–7.58 (m, 4H), δ 6.88 (br, 1H) δ 5.43 (s, 2H), δ 7.23 (q, J=6.3 Hz, 2H), δ 2.93(t, J=6.6, 2H)

Synthesis of Prodrug III (ortho)

To aldehyde 34 (0.216 g, 0.47 mmol) was dissolved in 2 ml of hot EtOH and then cooled to rt. To this solution was added thiosemicarbazide (47 mg, 0.52 mmol) in EtOH/H$_2$O (2.4 ml, 1:1) in one portion. After stirring at room temperature for 4 h, the mixture was stored in refrigerator (0°–5° C.) overnight. The mixture was then filtered and solid was rinsed with 2 ml of H2O, 2 ml of EtOH/H$_2$O (2:1) and 4 ml of ether to afford 35 (0.206 g, 82%) as white solid.

$^1$H NMR (CD$_3$OD, 300 MHz) δ 8.30–8.40 (m, 2H), δ 8.20 (s, 1H), δ 7.83 (dd, J=J=1.8, 7.2 Hz, 1H), δ 7.30–7.55 (m, 4 Hz, 1H), δ 5.41 (s, 2H), δ 3.59 (t, J=6.6, 2H), δ 2.98 (t, J=6.9, 2H)

Biological Activity

Balb/c mice were subcutaneously injected in the right flank on Day 0 with 0.2 mL of a 5×10$^6$ cell/mL suspension of M109 tumor cells which had been grown to log phase in culture, trypsin digested to separate, washed with PBS and reconstituted. Injections of 3-AP, Prodrug I (para), or Vehicle Control were given to the rats twice on Day 3, once a Day 4, twice on Day 6 and once on Day 7. Ten mice received only injections of 3-AP, each injection providing a dose of 4.5 mg/kg body weight. Ten mice received only injections of Prodrug I, each injection providing a dose of 10 mg/kg body weight. Ten mice received only injections of the vehicle control. The size of the tumors were measured by palpation on Days 7, 10, 13 and 17, and these results are presented in FIG. 10. This experiment clearly shows that Prodrug I is significantly more effective in reducing tumor growth than is an equal molar dose of 3-AP. In the case of FIG. 11, the anti-tumor effects of prodrug I (para) were compared to 3-AP using phosphate buffered saline (PBS) and aqueous dimethylsulfoxide (10% DMSO) as controls. In this experiment, prodrug I also evidenced superior anti-tumor activity compared to 3-AP or the two controls.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:

1. A compound according to the formula:

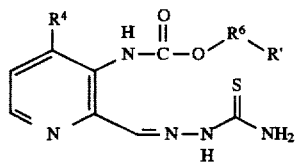

where

R$^4$ is H or CH$_3$ and

R$^5$ is CHR, benzyl or ortho or para substituted benzyl;

R is CH$_3$, CH$_2$CH$_3$, CH$_2$CH$_2$CH$_3$ or

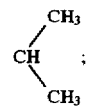

R' is a free acid phosphate, phosphate salt or an —S—S—R" group;

R" is CH$_2$CH$_2$NHR$^6$, CH$_2$CH$_2$OH, CH$_2$COOR$^7$, an ortho or para substituted C$_1$–C$_3$ alkylphenyl, or an ortho or para substituted nitro-phenyl;

R$^6$ is H, C$_1$–C$_4$ acyl group, trifluoroacetyl, benzoyl or substituted benzoyl group, and R$^7$ is H, C$_1$–C$_4$ alkyl, phenyl, substituted phenyl, or a benzyl or substituted benzyl.

2. The compound according to claim 1 where R$^5$ is CH$_2$.

3. The compound according to claim 1 where R$^5$ is

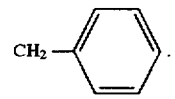

4. The compound according to claim 3 where R is CH$_3$.
5. The compound according to claim 1 where R$^4$ is H.
6. The compound according to claim 1 where R$^4$ is CH$_3$.
7. A compound according to the formula:

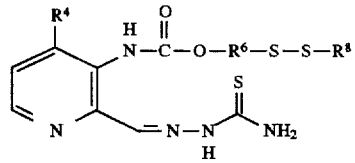

where

R$^4$ is H or CH$_3$, R$^5$ is CH$_2$ or

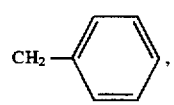

and

R$^8$ is CH$_2$CH$_2$NH$_2$, CH$_2$CH$_2$NHAc, CH$_2$CH$_2$OH or CH$_2$CO$_2$H.

8. The compound according to claim 7 where R$^4$ is CH$_3$.
9. The compound according to claim 7 where R$^4$ is H.
10. A method for treating neoplasia in animal or human patients, comprising; administering a therapeutically effective amount of a compound according to the formula:

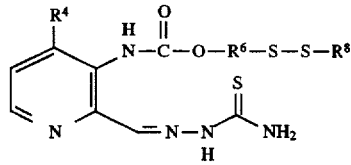

where $R^4$ is H or $CH_3$, $R^5$ is $CH_2$ or

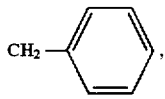

and $R^8$ is $CH_2CH_2NH_2$, $CH_2CH_2NHAc$, $CH_2CH_2OH$ or $CH_2CO_2H$.

11. The compound according to claim 10 where $R^4$ is $CH_3$.

12. The compound according to claim 10 where $R^4$ is H.

13. A method for treating neoplasia in animal or human patients comprising administering a therapeutically effective amount of a compound according to the formula:

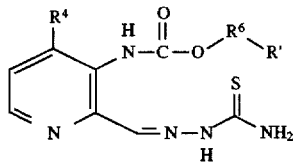

where
$R^4$ is H or $CH_3$ and
$R^5$ is CHR, benzyl or ortho or para substituted benzyl;
R is H, $CH_3$, $CH_2CH_3$, $CH_2CH_2CH_3$ or

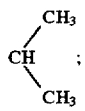

R' is a free acid phosphate, phosphate salt or an —S—S—R" group;

R" is $CH_2CH_2NHR^6$, $CH_2CH_2OH$, $CH_2COOR^7$, an ortho or para substituted $C_1$–$C_3$ alkylphenyl and ortho or para substituted nitro-phenyl;

$R^6$ is H, $C_1$–$C_4$ acyl group, trifluoroacetyl, benzoyl or substituted benzoyl group, and $R^7$ is H, $C_1$–$C_4$ alkyl or a benzyl or substituted benzyl.

14. The method according to claim 13 where $R^4$ is H or $CH_3$, and $R^6$ is $CH_2CH_2NH_2$, $CH_2CH_2NHAc$, $CH_2CH_2OH$ or $CH_2CO_2H$.

15. The method according to claim 13 where $R^4$ is H.

16. The method according to claim 13 where $R^4$ is $CH_3$.

17. The method according to claim 13 where $R^4$ is H or $CH_3$, $R^5$ is $CH_2$ or

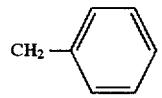

and $R^6$ is a para or ortho substituted nitrophenyl.

18. The method according to claim 17 where $R^4$ is H.

19. The method according to claim 17 where $R^4$ is $CH_3$.

20. The method according to claim 17 where $R^5$ is

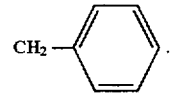

21. The method according to claim 17 where $R^5$ is $CH_2$.

* * * * *

UNITED STATES PATENT AND TRADEMARK OFFICE
CERTIFICATE OF CORRECTION

PATENT NO. : 5,767,134
DATED : July 16, 1998
INVENTOR(S) : Li et al.

It is certified that error appears in the above-identified patent and that said Letters Patent is hereby corrected as shown below:

On the title page, in the abstract, in the chemical structure, change "R6 " to --R5--.

Colum 3, lines 37-43, in the chemical structure, change " $R^6$ " to --$R^5$--.

In claim 1, lines 56-62, in the chemical structure, change " $R^6$ " to --$R^5$--.

In claim 7, lines 33-37, in the chemical structure, change " $R^6$ " to --$R^5$--.

In claim 10, lines 58-64, in the chemical structure, change " $R^6$ " to --$R^5$--.

In claim 13, lines 17-23, in the chemical structure, change " $R^6$ " to --$R^5$--.

Signed and Sealed this

Twenty-ninth Day of May, 2001

Attest:

NICHOLAS P. GODICI

*Attesting Officer*  *Acting Director of the United States Patent and Trademark Office*